United States Patent [19]

Hayakawa et al.

[11] 4,152,429

[45] May 1, 1979

[54] METHODS OF CONTROLLING PLANT FUNGI WITH COMPOSITIONS CONTAINING 2-CHLOROETHYLPHOSPHONIC ACID

[75] Inventors: Mitsuru Hayakawa; Mamoru Hayashi; Yasuo Kamuro, all of Tokyo, Japan

[73] Assignee: Amchem Products, Inc., Ambler, Pa.

[21] Appl. No.: 667,926

[22] Filed: Mar. 17, 1976

[51] Int. Cl.² ............................................. A01N 9/36
[52] U.S. Cl. .......................................... 424/222; 71/3; 71/86; 424/273 B; 424/274; 424/287; 424/300; 424/304
[58] Field of Search ............... 424/222, 273, 300, 287, 424/304, 309; 71/3, 86

[56] References Cited

U.S. PATENT DOCUMENTS

| | | | |
|---|---|---|---|
| 3,234,000 | 2/1966 | Bartels et al. | 71/3 |
| 3,701,799 | 10/1972 | Fancher | 71/3 |
| 3,745,187 | 7/1973 | Noguchi et al. | 424/300 X |
| 3,960,540 | 6/1976 | Crosby | 71/86 |

FOREIGN PATENT DOCUMENTS 1334850 10/1973 United Kingdom.

OTHER PUBLICATIONS

Chemical Abstracts 74: 139925b (1971).

*Primary Examiner*—Leonard Schenkman
*Attorney, Agent, or Firm*—Robert C. Brown

[57] ABSTRACT

Synergistic ethephon (2-chloroethylphosphonic acid) plus fungicide compositions applied to plants produce enhanced fungicidal activity and enhanced plant growth regulant activity.

2 Claims, No Drawings

METHODS OF CONTROLLING PLANT FUNGI WITH COMPOSITIONS CONTAINING 2-CHLOROETHYLPHOSPHONIC ACID

DETAILED DESCRIPTION OF THE INVENTION

This invention relates to ethephon fungicide compositions for agricultural and horticultural use. More particularly, it relates to compositions for agricultural and horticultural use obtained by adding 2-chloroethylphosphonic acid (hereinafter called ethephon) to a conventional agricultural fungicide to produce a composition with enhanced fungicidal activity and enhanced plant growth regulant activity. There are various types of excellent fungicides for controlling plant-diseases, for example, fruit tree-diseases, storage-diseases and soil diseases, have been developed and put to practical use. For example, methyl-1-(butylcarbamoyl)-2-benzimidazolecarbamate (Benomyl) having a penetrative fungicidal activity is effective on powdery mildew, black spot and soil disease, of fruit trees; and, 1,2-bis(3-ethoxycarbonyl-2-thioureido)benzene (hereinafter called thiophanate) is effective on leaf spot and black spot of fruit trees and storage disease of citrus. These two fungicides have no plant growth of regulant activity.

Ethephon itself is known as a plant growth regulator but shows little fungicidal activity when used alone, and is a compound having an extremely low toxicity.

Recently, soil pollution, residual toxicity, phytotoxicity on crops, atmosphere pollution and like pollutions in the natural environment which are caused by chemical-spraying pose important social problems.

In using fungicides and plant growth regulants such as ethephon, methods of reducing the use amount and the number of applications have been tried heretofore, but have not been yet put to practical use.

The present inventors have tried various investigations for the objects of reducing the use amount and the number of applications of general agricultural fungicides and controlling storage diseases and soil diseases. We have found that ethephon is effective as an extremely excellent synergist when used in general agricultural fungicides; further the fungicide may be acting as a synergist to the ethephon to enhance the plant growth regulant activity of ethephon.

The characteristics of the present invention are there even with half the amount of active ingredient of fungicide used practically heretofore and even with the half the number of applications a sufficient effect can be obtained. Effects on storage disease and soil disease can be extremely increased, by addition of a small amount of ethephon to fungicide used heretofore. Further addition of the fungicide to ethephon enhances the plant growth regulant activity, for example cucumber growth.

That is to say, according to the present invention the use amount of conventional fungicide can be greatly reduced, being preferable from the economical point of view and from the view-point of protecting the natural environment and the amount of ethephon used can be reduced and yet still obtain the beneficial effects of both.

In the present invention, the fungicides to be applied are not limited to benomyl and thiophanate described in the test examples, but can be used in combination with other fungicides, for example tetrachloro isophthalonitrile (chlorothalinol), cis-N-[(1,1,2,2-tetrachloroethyl)-thio]-4-cyclohexene-1,2-dicarboximide (captafol), manganese ethylene bis-dithiocarbamate (maneb).

Formulations which are tested in the test examples will be shown in the following, but they are not limited thereto.

| Formulation 1 | |
| --- | --- |
| Ethephon aqueous solution | |
| 2-chloroethyl phosphonic acid | 10 parts |
| water | 90 parts |

The above is homogeneously mixed to prepare an aqueous solution. This is used after dilution to a desired concentration with water.

| Formulation 2 | |
| --- | --- |
| Benomyl wettable powder | |
| Methyl-1-(butylcarbamoyl)-2-benzimidazolecarbamate | 50 parts |
| Clay | 35 parts |
| Carplex (Shionogi Pharmaceutical Co., Ltd.) | 10 parts |
| Sorpole 5039 | 2 parts |
| Lignin | 3 parts |

The above is homogeneously mixed and pulverized to prepare a wettable powder. This is used after dilution to a desired concentration with water.

| Formulation 3 | |
| --- | --- |
| Thiophanate wettable powder | |
| 1,2-bis(3-ethoxycarbonyl-2-thioureido)benzene | 70 parts |
| Clay | 10 parts |
| Carplex (Shionogi Pharmaceutical Co., Ltd.) | 15 parts |
| Sorpole 5039 | 2 parts |
| Lignin | 3 parts |

The above is homogeneously mixed and pulverized to prepare a wettable powder. This is used after dilution to a desired concentration with water.

Formulation 4

Ethephon combination (1) . . . benomyl wettable powder is diluted with water to a desired concentration and thereafter is added an ethephon aqueous solution so that a desired concentration of ethephon is obtained.

Formulation 5

Ethephon combination (2) . . . thiophanate wettable powder is diluted with water to a desired concentration and thereafter is added an ethephon aqueous solution so that a desired concentration of ethephon is obtained.

The present invention will be illustrated more concretely by following test examples, but is not limited thereto.

TEXT EXAMPLE 1

Test for leaf spot and black spot on pear trees

Nijisseiki young plants (3 years old) were tested under natural field conditions.

The test preparations used were prepared as follows:

(1) An aqueous solution (active ingredient: 167 ppm) obtained by diluting the benomyl wettable powder (Formulation 2) 3000 times with water.

(2) An aqueous solution (active ingredient: 84 ppm) obtained by diluting the benomyl wettable powder (Formulation 2) 6000 times with water.

(3) An aqueous solution (active ingredient: 20 ppm) obtained by diluting the ethephon aqueous solution (Formulation 1) 5000 times with water.

(4) A preparation obtained by diluting the benomyl wettable powder (Formulation 2) 3000 times with water and then by adding the ethephon aqueous solution (Formulation 1) so that the concentration of 2-chloroethylphosphonic acid is 20 ppm.

(5) A preparation obtained by diluting the benomyl wettable powder (Formulation 2) 6000 times with water and then by adding the ethephon aqueous solution (Formulation 1) so that the concentration of 2-chloroethylphosphonic acid is 20 ppm.

The preparations above described were sprayed on April 25 as the first application, and thereafter sprayed 10 times in intervals of 10 days. Test plots for spraying each of test preparations, (1), (2), (3), (4), and (5) as mentioned above were set up.

Four Nijisseiki young plants (3 years old) were used in each treatment, and each preparation was sprayed so that the whole plant body was uniformly wetted.

Observations for emergence of disease were made firstly after 5 days from the 7th application and secondly after 5 days from the 10th application on two twigs each having about 100 leaves (totally eight twigs in each treatment), and the numbers of infected leaves and healthy leaves were counted in order to determine the percentage of infected leaves.

$$\text{Percentage of infected leaves} = \frac{\text{Numbers of infected leaves}}{\text{Numbers of total leaves}} \times 100$$

The results are given in Table 1.

The test preparations given in Table 1 have the following meanings.

| | |
|---|---|
| benomyl × 3000 | Said preparation (1) is sprayed. |
| benomyl × 6000 | Said preparation (2) is sprayed. |
| ethephon alone | Said preparation (3) is sprayed. |
| benomyl × 3000 + ethephon | Said preparation (4) is sprayed. |
| benomyl × 6000 + ethephon | Said preparation (5) is sprayed. |

Table 1
percentage of infected leaves

| Test Preparations | Leaf Spot | | Black Spot | |
|---|---|---|---|---|
| | First | Second | First | Second |
| benomyl × 3000 | 2.1 | 4.4 | 0.2 | 2.6 |
| benomyl × 3000 + ethephon | 1.2 | 2.6 | 0.2 | 1.1 |
| benomyl × 6000 | 9.8 | 13.5 | 3.1 | 8.8 |
| benomyl × 6000 + ethephon | 4.3 | 6.1 | 1.6 | 2.2 |
| ethephon alone | 20.0 | 28.5 | 14.7 | 21.1 |
| Not sprayed | 23.6 | 38.7 | 17.6 | 29.2 |

As shown in Table 1, little controlling effect is observed in the ethephon treatment, but a remarkable reinforcing effect can be obtained with the combination of ethephon plus benomyl. The practical concentration of benomyl is that of benomyl×3000, however an equivalent effect with that obtained in the benomyl×3000 treatment can be obtained at half the concentration of benomyl×3000 when ethephon is used in combination.

TEST EXAMPLE 2

Test For Leaf Spot of Pear

Nijisseiki young plants (3 years old) were used as in the Test Example 1, and the test was carried out under natural field conditions. Further, the test was conducted by extending the intervals between applications, that is, by reducing the numbers of applications during the period of one season. Spraying of preparations was started on April 25th, and thereafter the preparations were sprayed 10 times at intervals of 10 days, and in another case the preparations were sprayed on April 25th for the first time and thereafter sprayed 5 times at intervals of 20 days. As test preparation, there were used the preparations (1), (3) and (4) described in Test Example 1.

Spraying of the test preparations and observation of the numbers of infected leaves were conducted in the similar way as in the Test Example 1. Observation was made only for leaf spot. Further, observations were made 5 days after the 10th application for the 10 applications and 5 days after the 5th applications, for the 5 applications and the percentage of infected leaves was determined as in the Test Example 1. The results are given in Table 2.

Each test preparation given in Table 2 has the following meaning. Benomyl×3000, sprayed 10 times ... The test preparation (1) is sprayed 10 times at intervals of 10 days. Benomyl×3000, sprayed 5 times ... The test preparation (1) is sprayed 5 times at intervals of 20 days. Benomyl×3000+ethephon, sprayed 5 times ... The test prepration (4) is sprayed 5 times at intervals of 20 days. Ethephon sprayed 5 times ... The test preparation (3) is sprayed 5 times at intervals of 20 days.

Table 2

| Test Preparations | Percentage of Infected Leaves |
|---|---|
| Benomyl × 3000, sprayed 10 times | 4.4 |
| Benomyl × 3000, sprayed 5 times | 14.2 |
| Benomyl × 3000 + ethephon, sprayed 5 times | 4.6 |
| Ethephon, sprayed 5 times | 30.0 |
| Not Sprayed | 38.7 |

As shown in Table 2, 10 applications per one season are required for Benomyl, and the percentage of infected leaves is greatly increased when the number of applications is reduced to 5. It was observed that even 5 applications gave a sufficient effect when benomyl was used in combination with ethephon having little fungicidal activity according to the present invention.

TEST EXAMPLE 3

Test for Controlling the Storage Disease of Citrus

As rotteness-preventing agent for mandarin oranges, thiophanate, ethephon and a mixture of thiophanate and ehtephon were tested. The test preparations were prepared in the following manner.

(1) Thiophanate wettable powder (Formulation 3) is diluted 1500 times with water to prepare an aqueous solution (active ingredient: 470 ppm).

(2) Ethephon aqueous solution (Formulation 1) is diluted 500 times with water to prepare an aqueous solution (active ingredient: 200 ppm). (3) Thiophanate wettable powder is diluted 1500 times with water, and to the resulting aqueous solution is added the ethephon aqueous solution sot that the concentration of 2-chloroethylphosphonic acid is 200 ppm.

Each preparation was applied on November 10th, the fruits were harvested on November 17th, and the fruits were packed in a small corrugated cardboard box every 1000 fruits and stored in a room at room temperature.

Three small corrugated cardboard boxes containing 100 oranges treated with said test preparation were used in each test. At intervals of definite days after the start of storage the numbers of rotten fruits were determined by visual observation. The results are given in Table 3.

Test preparations in Table 3 have the following meanings. Thiophanate alone ... Said test preparation (1) is applied. Ethephon alone ... Said test preparation (2) is applied. (Thiophanate+Ethephon) ... Said test preparation (3) is applied.

Table 3

Percentage of Rotten Fruits

| Test Preparations | Days After the Start of Storage | | | | |
|---|---|---|---|---|---|
| | 14 days | 21 days | 28 days | 35 days | 42 days |
| Thiophanate alone | 0 | 0.8 | 3.4 | 5.2 | 7.4 |
| Thiophanate + ethephon | 0 | 0.6 | 1.9 | 3.1 | 4.0 |
| Ethephon alone | 0 | 3.8 | 6.2 | 7.1 | 9.3 |
| Not treated | 0 | 4.1 | 7.3 | 9.8 | 11.2 |

*Note:
Percentage of rotten fruits represents the mean value of the rotten fruits in 3 boxes.

$$\text{Percentage of rotten fruits} = \frac{n_1 + n_2 + n_3}{3 \times 100} \times 100$$

$n_1$, $n_2$, and $n_3$: the numbers of rotten fruits in each box.

As shown in Table 3, the percentage of rotten fruits becomes 4% about 21 days after the start of storage for the control (not treated) and "ethephon alone", whereas about 30 days for "Thiophanate alone" and about 42 days for "Thiophanate+Ethephon". Therefore, a remarkable effect can be obtained by use of thiophanate in combination with ethephon.

TEST EXAMPLE 4

Test For Controlling Canker of Cucumber

Each one cucumber seedling (kind: Aonagachibai) was reared in a pot of 10 cm diameter, and then planted into a Wagner pot of $1/5000_a$ in the one-expanded leaf stage. In the Wagner pot of $1/5000_a$ was placed a soil containing canker-causing fungus which was cultivated in soil mixed with bran. Benomyl wettable powder (Formulation 2) was used as test preparation. This Benomyl wettable powder was diluted 1000 times, and each 50 ml of the resulting dilution was poured to the rearing pot 5 days prior to transplantation, and immediately after transplantation 200 ml of said dilution was poured to the Wagner pot of $1/5000_a$. On the other hand, the ethephon aqueous solution (Formulation 1) was added to the 1/1000 dilution of Benomyl wettable powder so that the concentration of 2-chloroethylphosphonic acid was 50 ppm. Thus obtained solution was poured in a similar way as said Benomyl wettable powder.

For ethephon treatment, the ethephon aqueous solution (Formulation 1) was diluted 2000 times with water, and the resulting dilution was applied 4 times, 5 days prior to transplantation, immediately after transplantation, 2 weeks after transplantation and 4 weeks after transplantation in such a manner that the whole plant body of cucumber was uniformly wetted.

Test was conducted using 3 pots per one treatment and using 4 seedlings per one pot.

Investigations on emergence of disease and growth state were made 40 days after transplantation. The percentage of disease emergence was calculated by the following equation:

$$\text{Percentage of disease emergence} = \frac{2 \times n_1 + 1 \times n_2 + 0 \times n_3}{2 \times (n_1 + n_2 + n_3)} \times 100$$

$n_1$: numbers of dead plants
$n_2$: numbers of plants that browning was observed in vessel
$n_3$: numbers of healthy plants The percentage of dead plants was calculated by the following equation:

$$\text{Percentage of dead plants} = \frac{\text{Numbers of dead plants}}{\text{Numbers of tested plants}} \times 100$$

For the growth state of cucumber, the investigation was made on the plants which showed healthy growth state, with regard to leaf-stage, height, and the numbers of nodes bearing female flowers. The results are given in Table 4.

Table 4

| Test Preparations | Emergence of disease | | Investigation of growth state | | |
|---|---|---|---|---|---|
| | % of dead plants | % of disease emergence | Leaf Stage | Height (cm) | Nos. of nodes bearing female flowers |
| Benomyl | 23.8 | 42.8 | 20.7 | 111.4 | 4.8 |
| Benomyl + Ethephon | 12.2 | 21.0 | 17.7 | 92.0 | 12.0 |
| Ethephon | 71.5 | 80.8 | 17.2 | 81.2 | 11.6 |
| Not treated | 84.4 | 91.3 | 16.1 | 78.0 | 4.5 |

As shown in Table 4, it is observed that the percentage of dead plants and percentage of disease emergence are reduced by half in the combined use of benomyl with ethephon, as compared in the treatment with benomyl alone.

As for the growth state, it is observed that ethephon has a female flower-bearing activity as is well known and that this activity is not injured by the use of ethephon is combination with benomyl and is in fact enhanced somewhat.

What is claimed is:

1. A method of enhancing the plant growth regulating effect of 2-chloroethylphosphonic acid and the resistance of pear trees including their fruits to leaf spot and black spot by applying to the plant an effective amount, having regard to the plant being treated of a composition consisting essentially of about 20 parts per million of 2-chloroethylphosphonic acid and about 84 parts per million of methyl-1-(butylcarbamoyl)-2-benzimidazolecarbamate.

2. A method of enhancing the plant growth regulating effect of 2-chloroethylphosphonic acid and the resistance of pear trees including their fruits to leaf spot and black spot by applying to the plant an effective amount, having regard to the plant being treated of a composition consisting essentially of about 20 parts per million of 2-chloroethylphosphonic acid and about 167 parts per million of methyl-1-(butylcarbamoyl)-2-benzimidazolecarbamate.

* * * * *